United States Patent [19]

Rolfe et al.

[11] Patent Number: 5,008,194

[45] Date of Patent: Apr. 16, 1991

[54] NIFH PROMOTERS OF BRADYRHIZOBIUM

[75] Inventors: Barry G. Rolfe, Curtin; John Shine, Sydney; Kieran F. Scott, Page, all of Australia; Hauke Hennecke, Zurich, Switzerland

[73] Assignee: Lubrizol Genetics, Inc., Wickliffe, Ohio

[21] Appl. No.: 109,869

[22] Filed: Oct. 16, 1987

Related U.S. Application Data

[63] Continuation-in-part of Ser. No. 618,439, Jun. 8, 1984, abandoned, and a continuation-in-part of Ser. No. 900,270, Aug. 26, 1986, abandoned, which is a continuation of Ser. No. 506,676, Jun. 22, 1983, abandoned.

[51] Int. Cl.$^5$ .................... C12N 15/00; C12R 1/41; C07H 15/12
[52] U.S. Cl. .................. 435/172.3; 435/252.2; 435/252.3; 435/320.1; 536/27; 935/6; 935/35; 935/41
[58] Field of Search ............. 435/172.3, 320, 68, 435/70, 253, 252.2, 252.3; 935/30, 35, 6, 41

[56] References Cited

U.S. PATENT DOCUMENTS 4,803,165  2/1989  Appelbaum .................. 435/68

OTHER PUBLICATIONS

Kaluza et al., 1985, Febs Letters 188(1): 37–42.
Watson et al., 1985 Mol. Gen. Genet. 199: 279–289.
Alvarez-Maroles, A. and Hennecke, H. (1985) Mol. Gen. Genet. 199:306–314.
Thony, B. et al. (1985) Mol. Gen. Genet. 198:441–448.
Kaluza, K. et al. (1985) Adv. Mol. Genet. Bact.-Plant Interact. Proc. Int. Symp. 2nd, Jun. 4–8, 1984, pp. 32–33.
Kaluza, K. et al. (1985) Fed. Eur. Biochem. Soc. 188:37–42.
Hahn, M. et al. (1984) Chemical Abstracts 100(15):124–Ref. No. 115675z.
Simon, R. et al. (1983) Bio/Technol. 9:784–791.
Ruvkun, G. B. et al. (1981) Nature 289:85–88.
Scott, K. F. (1986) Nucl. Acids Res. 14:2905–2915.
Shine, J. and Dalgarno, L. (1974) Proc. Natl. Acad. Sci. USA 71:1342–1346.
Fuhrmann, M. and H. Hennecke (1984) J. Bact. 158:1005–1011.
Adams, T. H. and B. K. Chelm (1984) J. Molec. & Appl. Genet. 2:392–405.
Lippman D. and W. R. Pearson (1985) Science 227:1435–1441.
Legocki, R. P. et al. (1984) Proc. Natl. Acad. Sci. USA 81:5806–5810.
Beynon, J. et al. (1983) Cell 34:665–671.
Better, M. et al. (1983) Cell 35:479–485.
Adams, T. H. and B. K. Chelm (1984) J. Molec. & Appl. Genet. 2:392–405.
Noti, J. D. et al. (1986) J. Bact. 167:774–783.
Sundaresan, V. et al. (1983) Nature 301:728–732.
Better, M. et al. (1983) Cell 35:479–485.

Primary Examiner—Elizabeth C. Weimar
Assistant Examiner—David T. Fox
Attorney, Agent, or Firm—Greenlee and Associates

[57] ABSTRACT

The nifH promoter regions of Bradyrhizobium japonicum and Bradyrhizobium sp. (parasponia) have been sequenced and found to be significantly homologous. Recombinant DNA molecules comprising foreign genes under the control of such promoters are provided. Rhizobial species containing such recombinant constructions, either in plasmids or integrated into the genome, are provided. These are especially useful for expressing desired foreign genes within root nodules.

7 Claims, 2 Drawing Sheets

FIG. 1

```
5'- T T A G T G C T - C A T G A G A C C C T G G C A T G C C G G T T G C A A G T C T T T G G A T C A A G A A G...37bp...ATG...Rj nifD
     A A G G T G C C G G G T T A G A C C C T G G C A C G G C C G G T T G C C T T G C T A T G G C A G C A A C A C...143bp...ATG...Rj nifH
     T A A T A A G C G G C G G G A C A G T G T T G G C A T G C C G A T T G C A T T G C T G A G T T G C A G C A A C A C...142bp...ATG...RP nifH
     T A G T T T T A T T T C A G A C G G T T G G C A A C G C C G T T G C T T T C C T A C G A T C A A G G G C A A A C G G...62bp...ATG...Rm nifH
     A T A C A T A A T G C C A A A G C A C G G T T G G T A T G C C G T T G C T T T C G A T C C C T G G G C A A A C G A...22bp...ATG...Kp nifH
     G C G G T A G T G C C G G T A C G C C G T T G G G T C A C G C C A C T G C A T T G C T G A G T T C C G A G A A C G C...35bp...ATG...Kp niff
     T C T T G C C A C C A T C C C G T A A C G C C G T A G G G C G C G G G C A T T G C A T C C G T T C G G A...65bp...ATG...Kp nifL
```

FIG. 2

NIFH PROMOTERS OF BRADYRHIZOBIUM

CROSS REFERENCE TO RELATED APPLICATIONS

This application is a continuation-in-part application of co-pending application no. 900,270 filed Aug. 26, 1986, now abandoned, which is a continuation of Ser. No. 506,676 filed June 22, 1983, now abandoned. This application is also a continuation-in-part application of application Ser. No. 618,439 filed June 8, 1984, now abandoned, all the foregoing applications being incorporated herein by reference.

FIELD OF THE INVENTION

This invention lies in the field of genetic engineering, particularly recombinant DNA constructions using novel promoter sequences.

BACKGROUND OF THE INVENTION

Early literature references to Rhizobium japonicum refer to strains characterized as "slow-growing" Rhizobia. More recent studies of biochemical and genetic characteristics have led to reclassification of "slow-growing" Rhizobia in the genus Bradyrhizobium (Jordan, D. C. (1982) Int. J. Syst. Bacteriol. 32:136). Furthermore, certain "fast-growing" strains have been found which are classified as R. japonicum on the basis of their ability to nodulate Glycine Max cv. Peking, an undeveloped Asian cultivar of soybean. Since the literature sometimes refers to slow-growing (Bradyrhizobium) strains simply as R. japonicum, confusion may occur. For clarity herein, "slow-growing" soybean nodulating strains are termed *Bradyrhizobium japonicum* strains, while "fast-growing" strains are termed *Rhizobium japonicum* strains. Similarly, (Parasponia) Rhizobium sp. has been reclassified as Bradyrhizobium sp. (Parasponia) (see, e.g. Scott, K. F. (1986), "Conserved nodulation genes from the non-legume symbiont Bradyrhizobium sp. (Parasponia)," Nucl. Acids Res. 14:2905-2919), and will be so referred to herein, although prior art references may specify the former name.

Biological nitrogen fixation in the root nodules of leguminous plants is a major component of world food production and therefore practical applications of this field are of major interest.

Prokaryotes can use a wide variety of nitrogen compounds as sole sources of cellular nitrogen. This variety includes ammonia, dinitrogen and nitrate among the inorganic compounds, and proline, arginine and glutamine among complex organic compounds. Each species can utilize a different array of nitrogen compounds. Glutamine, glutamate and aspartate are the key nitrogen compounds in intermediary metabolism. The latter two are the starting compounds of many pathways of amino acid biosynthesis and serve as amino group donors in many reactions. In all other cases the amino group is donated by glutamine. The major enzyme required for the assimilation of ammonia produced by N₂ fixation is glutamine synthetase, which catalyses the reaction:

Glutamate+NH₃+ATP→glutamine+ADP+Pi.

At high $NH_4^+$ concentrations (>1 mM) glutamate dehydrogenase is also found. Utilization of the assimilated ammonia depends on the activity of glutamate synthase catalyzing:

Glutamine+2-ketoglutarate+NADPH→2-glutamate+NADP+

Since ATP is hydrolysed, these reactions have a favorable equilibrium and allow the use of ammonia in the medium or ammonia derived enzymatically from other nitrogen sources (Meers, J. et al. (1970) J. Gen. Microbiol. 64:187-194). The formation of ammonia is thus a key step in the biological nitrogen cycle.

Biological nitrogen fixation can be achieved by a variety of microorganisms and occurs through the induction of an enzyme complex, nitrogenase, which converts atmospheric nitrogen to ammonia. This conversion occurs in a group of physiologically diverse prokaryotes, including facultative anaerobes (e.g., *Klebsiella pneumoniae* and *Rhodosoirillum rubrum*), obligate anaerobes (e.g., *Clostridium pasteurianum*), obligate aerobes (e.g., *Azotobacter vinelandii*) and some strains of blue-green algae (e.g., *Anabaena cylindrica*) (Sprent, J. I. (1979) The Biology of nitrogen fixing organisms, London, McGraw-Hill, pp. 8-11). While this enzyme complex is common to all characterized nitrogen fixing organisms, the conditions under which it is expressed vary considerably between species (Burns, R. C., Hardy, R. W. F. (1975) Nitrogen fixation in bacteria and higher plants, Springer-Verlag, Berlin). The first stages of nitrogen fixation, conversion of nitrogen into ammonia, are achieved symbiotically in the root nodules of leguminous plants which contain the nitrogen-fixing bacteria of the genera Rhizobium and Bradyrhizobium. Some non-leguminous plants, e.g., alder, also have interactions with symbiotic bacteria which are nitrogen fixers. In addition, free-living bacteria, e.g., *Klebsiella pneumoniae* and the photosynthetic blue-green bacteria, also fix nitrogen.

The symbiotic association between plants and bacteria of the genera Rhizobium and Bradyrhizobium is the result of a complex interaction between the bacterium and its host, requiring the expression of both bacterial and plant genes in a tightly coordinated manner (Vincent, J. M. (1980) In Symbiotic Associations and Cyanobacteria, Nitrogen Fixation Vol. 2 (W. E. Newton, W. H. Orme-Johnson, eds. Baltimore, University Park Press pp. 103-129; and Verma, D. P. S. et al. (1981In Current Perspectives in Nitrogen Fixation (A. H. Gibson, W. E. Newton, eds.) Canberra: Australian Academy of Science, pp. 205-208). In free-living rhizobial organisms, nitrogenase synthesis is repressed and is only induced after the symbiotic relationship has been established. Furthermore, some species only interact with a narrow range of plant species, whereas other species interact with a wide range.

Bacteria bind to the emerging plant root hairs and invade the root tissue through the formation of an infection thread. The plant responds to this infection by the development of a highly differentiated root nodule. These nodules are the site of synthesis of the nitrogenase complex. Following nitrogen fixation, the fixed nitrogen is exported into the plant tissue and assimilated by the plant derived enzymes (Scott, D. B. et al. (1976) Nature 263:703,705).

Most rhizobial (this term includes Rhizobia and Bradyrhizobia) symbioses are confined to leguminous plants. Furthermore, strains which fix nitrogen in association with the agriculturally-important temperate legumes are usually restricted in their host range to a single legume genus. However, some rhizobial strains have been isolated which can fix nitrogen in a diverse group of legume species but can also form an effective symbiosis with non-legumes.

Despite the ability of certain plants to induce nitrogenase activity in a symbiotic relationship with some rhizobial species, the genetic analysis of biological nitrogen fixation has previously been confined to free living nitrogen fixing organisms, in particular *Klebsiella pneumoniae*. There are 17 linked nitrogen fixation (nif) genes arranged in at least 7 transcriptional units in the nif cluster of Klebsiella (Kennedy, C. et al. (1981) In *Current Perspectives in Nitrogen Fixation* (A. H. Gibson, W. E. Newton, eds.) Canberra: Australian Academy of Science, pp. 146–156; and Reidel et al. (1979) Proc. Nat. Acad. Sci. U.S.A. 76:2866–2870). Specific designations are assigned to nif genes, e.g. nifH, based on structural homologies to previously identified genes in other nitrogen fixing organisms at the DNA and protein levels. Three of the Klebsiella genes, nifH, nifD and nifK encode the structural proteins of the nitrogenase enzyme complex (viz. the Fe-protein subunit (dinitrogenase reductase) and the $\alpha$- and $\beta$-subunits of the Mo-Fe protein (dinitrogenase) respectively). Dinitrogenase is an $\alpha_2\beta_2$ tetramer in which the two non-identical $\alpha$ and $\beta$ subunits have similar molecular weights of 55,000 to 60,000. Dinitrogenase reductase is a dimer of two identical subunits each having a molecular weight around 35,000. These genes are linked in the same operon in K. pneumoniae and are transcribed from a promoter adjacent to the nifH gene. A similar situation (nifHDK) was found in two fast-growing rhizobia, R. meliloti (Ruvkun, G. B. et al. (1982) Cell 29:551–559) and R. leguminosarum (Schetgens, T. M. P. et al. (1984) "Identification and analysis of the expression of *Rhizobium leguminosarum* PRE symbiotic genes", p. 699, In C. Veeger and W. E. Newton (eds.) *Advances in Nitrogen Fixation Research*, Martinus Nijhoff/Dr. W. Junk Publishers, The Hague). In the slow-growing B. japonicum, it has been found that nifDK forms one operon and that nifH is located elsewhere on the genome (Fuhrmann, M. and H. Hennecke (1982) Mol. Gen. Genet. 187:419–425). A similar observation was made with another member of the slow-growing rhizobia, Rhizobium, sp. (Parasponia): a nifH region was found not to be linked to nifD (Scott, K. F. et al. (1983) DNA 2:141–148). Yet a different arrangement was detected in the cyanobacterium Anabaena sp. 7120, in which nifHD is separated from nifK (Rice, D. et al. (1982) J. Biol. Chem. 257:13157–13163). The remainder of symbiotic genes contain information required for bacterial attachment, root hair curling, initiation and development of nodules and establishment of symbiotic relationships. In addition, regulatory sequences such as promoters, operators, attenuators, and ribosome binding sites are found adjacent to the coding regions. These regulatory sequences control the expression of the structural genes, i.e., the coding sequences downstream in the 3'-direction of the DNA reading strand.

In rhizobia, nitrogenase synthesis is normally repressed under free-living conditions and is induced only within a complex symbiosis formed mostly with leguminous plants. R. trifolii is an example of a fast-growing Rhizobium with a narrow host range which cannot normally be induced to fix nitrogen in culture. In contrast, a Bradyrhizobium sp. (Parasponia) species has been isolated and this species is a slow-growing organism with a very broad host range capable of an effective symbiotic relationship with a broad variety of tropical legumes as well as the non-legume Parasponia (Ulmaceae) (Trinick, M. J. (1980) J. Appl. Bacteriol. 49:39–53). Bradyrhizobium sp. (Parasponia) can be induced to fix nitrogen in culture although the level of this fixation is about 100-fold less than can be obtained from the free-living bacterium *Klebsiella pneumoniae*. Other slow-growing rhizobia (Bradyrhizobia) include the commercially significant *Bradyrhizobium japonicum*, which nodulates soybeans.

The genetics of biological nitrogen fixation have been well characterized in the free-living organism *Klebsiella pneumoniae*. The structural genes for nitrogenase nifH, nifD and nifK encoding the Fe-protein subunit and the $\alpha$ and $\beta$ subunits of the Mo-Fe protein, respectively have been mapped both genetically and physically (Kennedy, C. et al. (1981) In *Current Perspectives in Nitrogen Fixation* (eds. Gibson, A. H. and W. E. Newton) Australian Acad. Science, Canberra, pp. 146–156; and Reidel, G. E. et al. (1979), Proc. Nat. Acad. Sci. U.S.A. 76:2866–2870). Cloned DNA fragments carrying these sequences have been shown, by Southern blot analysis, to hybridize to homologous sequences in a wide range of nitrogen fixing organisms, including rhizobial species (Ruvkun, G. B. and F. M. Ausubel (1980) Proc. Nat. Acad. Sci. U.S.A. 77:191–195).

In spite of the ecological diversity of nitrogen fixing organisms, the physiological structure of the nitrogenase enzyme complex appears to be very conserved. In all cases where the enzyme complex has been purified, two proteins are present. The larger protein (dinitrogenase) contains molybdenum, iron and acid-labile sulfur, and carries the binding site for nitrogen and contains two subunit proteins $\alpha$- and $\beta$-coded by the nifD and nifK genes respectively. The smaller protein (dinitrogenase reductase) contains iron and acid-labile sulfur, and is required for the reduction of the dinitrogenase and for the binding of MgATP used in this reduction. The dinitrogenase reductase is coded by the nifH gene. Chemical and spectral analyses of the purified protein components support a conservation of protein structure between organisms (Scott, K. F. et al. (1981) J. Mol. Appl. Genet. 1:71–81). In some cases the structures are sufficiently similar to allow formation of active hybrid enzymes between purified components, e.g., *Azotobacter vinelandii* and *Klebsiella pneumoniae* (Eady, R. R. and B. E. Smith (1979) In: *A treatise on dinitrogen fixation* I, II, eds. Hardy, R. W., Bottomley, F. and R. C. Burns, New York, Wiley Press pp. 399–490). Not surprisingly, therefore, the region of the operon coding for dinitrogenase reductase and dinitrogenase $\alpha$-subunit (nifH and nifD) shows homology at the nucleic acid sequence level with the corresponding sequences in at least 19 other bacterial strains (Ruvkun, G. B. and F. M. Ausubel (1980) Proc. Nat. Acad. Sci. U.S.A. 77:191–195). Although this conservation of structure is generally true, significant differences between nitrogenases from different organisms also exist as can be shown by variable stability following purification and by the fact that active hybrid complexes do not form in all cases (Eady, R. R. and B. E. Smith (1979) supra).

A DNA fragment carrying the *Klebsiella pneumoniae* nifK, nifD and nifH genes has been isolated from the nif-strain UNF841(Tn5:nifK) (Cannon, F. C. et al. (1979) Mol. Gen. Genet. 174:59–66) and cloned into the *Escherichia coli* plasmid pBR325. The nucleotide sequences of the nifH gene and of 622 nucleotides of the nifD gene were determined (Sundaresan, V. and F. M. Ausubel (1981) J. Biol. Chem. 256:2808–2812; Scott, K. F. et al. (1981) supra). In addition, the DNA sequence of the nifH gene from Anabaena 7120 has been determined (Mevarech, M. et al. (1980) Proc. Nat. Acad. Sci. U.S.A. 77:6476–6480). A comparison of the two nucleotide sequences demonstrates two interesting features: (1) There is very little homology between the two sequences although a few stretches (up to 25 bp) are conserved, accounting for the observed interspecies homology of the nif genes (Ruvkun, G. B. and F. M. Ausubel (1980) supra); (2) In general, the promoter regions show very little sequence homology with the exception of a short region likely to be involved in common functions, e.g., RNA polymerase recognition.

In contrast, a comparison of the amino acid sequences of the dinitrogenase reductase and of the first 207 amino acids of the α-subunit of dinitrogenase of the two species and of another species show a much greater conservatism. The three species used in this comparison are Klebsiella pneumoniae (Kp); Anabaena 7120 (Ab); and Clostridium asteurianum (Cp) (Tanaka, M. et al. (1977) J. Biol. Chem. 252:7093–7100). The Kp and Cp proteins share 67% amino acid sequence homology, Kp and Ab proteins share 71% homology, and the Cp and Ab proteins share 63%. This amino acid sequence homology is not spread evenly throughout the protein. Some regions are virtually identical (90% to 95% homology), while other regions are only weakly conserved (30–35% homology). The structural conservation appears to be centered around the five cysteine residues common to all three Fe proteins. These cysteine residues are believed to be ligands to the active center. Comparison of the N-terminal amino acid sequence of the α-subunit of dinitrogenase from Cp and Kp shows very little sequence homology in this region. This is in contrast to the very high conservation of amino acid sequence seen in the amino terminal region of the Fe protein. What little homology exists between Cp and Kp α-subunits is confined to regions around cysteine residues, as in the Fe proteins. These homologous regions are thought to be involved in the catalytic functions of the nitrogenase enzyme complex. Therefore, this structural conservatism is thought not to be the result of recent evolution and dispersal of the nif genes (Postgate, J. R. (1974) Sym. Soc. Gen. Microbiol. 24:263–292) but, rather, is postulated to be related to a conservation of function.

The discovery and study of plasmids, restriction enzymes, ligases and other enzymes involved in DNA synthesis has led to the rapidly developing field of genetic engineering. Use of these techniques has made it possible to transfer DNA across species boundaries, either from eukaryotic to prokaryotic organisms or vice versa. Alternatively, it has been possible to synthesize nucleotide sequences and to incorporate these synthetic sequences into living organisms where they have been expressed. For example, expression in E. coli has been obtained with DNA sequences coding for mouse dihydrofolate reductase (Chang, A. C. Y. et al. (1978) Nature 275:617–624) and for hepatitis B virus antigen (Burrell, C. J. et al. (1979) Nature 279:43–47). Two mammal hormones have also been produced in bacteria by use of synthetic DNA (Itakura, K. et al. (1977) Science 198:1056; and Goeddel, D. B. et al. (1979) Proc. Nat. Acad. Sci. U.S.A. 76:106). The practical application of DNA recombination requires the success of a number of different features. First, it must be possible to recognize the DNA fragment coding for the compound of interest and it must be possible to isolate that DNA fragment. Second, it is necessary to understand the mechanisms which control the expression of the information on that DNA fragment and to be able to transfer that information to the control of regulatory sequences which will maximize the productive capabilities of that information. This increased productive capacity could be by rearrangement of coding information and regulatory information within the same organism or between different organisms. The organisms involved may be prokaryotic or eukaryotic. Third, the conversion of coding information into useful products, such as storage proteins and hormones, must occur in an environment where they are not subsequently degraded.

In many cloning projects, only one of the two DNA strands is required initially. Many techniques have been used including poly(UG)-CsCl gradients (Szybalski, W. et al. (1971) Methods Enzymol., Grossman, L., and Moldave, K., eds. Vol.21D Academic Press, New York pp. 383–413), polyacrylamide gels (Maxam, A. and W. Gilbert (1977) Proc. Nat. Acad. Sci. U.S.A. 74:560–564), and exonuclease treatment (Smith, A. J. H. (1979) Nucl. Acids. Res. 6:831–848). An alternative biological approach has been developed using the bacteriophage M13. The replicative form of this phage DNA is a circular double stranded molecule; it can be isolated from infected cells and used to clone DNA fragments after which it can be reintroduced into *Escherichia coli* cells by transfection. M13 phage particles each containing a circular single stranded DNA molecule are extruded from infected cells. Large amounts of single stranded DNA containing a cloned fragment (5–110 μg phage DNA/ml bacterial culture) can be easily and quickly recovered (Messing, J. et al. (1977) Proc. Nat. Acad. Sci. U.S.A. 74:3642–3646). The cloning of DNA fragments into the replicative form of M13 has been facilitated by a series of improvements which led initially to the M13mp7 cloning vehicle (Messing, J. et al. (1981) Nucleic Acids Res. 9:309–321). A fragment of the E. coli lac operon (the promoter and N-terminus of the β-galactosidase gene) was inserted into the M13 genome A small segment of DNA containing a number of restriction cleavage sites was synthesized and inserted into the structural region of the β-galactosidase fragment. The M13mp7 DNA remains infective and the modified lac gene can still encode the synthesis of a functional β-galactosidase α-peptide.

Following M13mp7, two new single stranded DNA bacteriophage vectors M13mp8 and M13mp9, have been constructed (Messing, J. and J. Vieria (1982) Gene 19:269–276). The nucleotide sequence of M13mp7 has been modified to contain only one each of the restriction sites (instead of two) and single restriction sites for HindIII, SmaI and XmaI have been added. Thus the restriction sites are EcoRI-SmaI-XmaI-BamHI-SalI-AccI-HincII-PstI-HindIII. These restriction sites have opposite orientations in M13mp8 and M13mp9. DNA fragments whose ends correspond to two of these restriction sites can be "force cloned" to one or the other of these two M13 cloning vehicles which have also been "cut" by the same pair of restriction enzymes. Thus a DNA fragment can be directly oriented by forced cloning. This procedure guarantees that each strand of the cloned fragment will become the (+) strand in one or the other of the clones and will be extruded as single stranded DNA in phage particles.

Restriction endonuclease cleavage fragments with noncomplementing ends are seldom joined in a ligation.

DNA cleaved by two different restriction endonucleases therefore cannot be circularized nor joined to another fragment produced by the same "two different restriction endonucleases" in both orientations. The result is that a recombinant molecule is formed during the ligation reaction with a defined order of the two fragments. Since the orientation of a cloned DNA fragment in the replicative form of M13 vectors determines which of the two DNA strands is going to be the viral strand, the use of M13mp8 or M13mp9 allows the direct preparation of one of the two DNA strands by cloning.

SUMMARY OF THE INVENTION

This invention provides useful rhizobial promoters for the construction of recombinant molecules to regulate foreign genes for expression under desired conditions. In particular, the promoters act to control expression of the foreign genes within root nodules formed by rhizobial bacterial strains in symbiotic combination with host plants.

A recombinant DNA molecule is provided comprising:

(a) A regulatory region or promoter of a nifH gene selected from the group consisting of Bradyrhizobium sp. (Parasponia) and *Bradyrhizobium japonicum* nifH genes; and (b) a foreign structural gene under control of said promoter.

The promoter is capable of activating expression of a nifH gene, preferably the nifH gene it activates in nature, in a nodule of a plant, preferably soybean or siratro, and has a nucleotide sequence selected from the group consisting of:

(1) functional promoter sequences comprised within the sequence of the Bradyrhizobium sp. (Parasponia) nifH promoter as follows:

5' ... CCG CGC AGA TCC TGT CCG GTG CAA ACC TCC

CTG GGG TAG CTC AGC GGC TCG TTG GCT TTT

TAG AGC GTA ATC AAG AAG CTT AAT AAG CGC

GGA CAG TGT TGG CAT GGC GAT TGC TGT TGA

GTT GCA GCA ACA CTG AGT GAG GGC TGG GTG

CAC GCC GAC GCG TAA GAC GAG CGA TGC GCT

CCT TCC CTT GAA CCC GTG TGC CCC GTT TCT

GAG AGA GAA ACA AGC TCG CGT GTC GGA AGC

ACG CAA CTT TTG GCA AAT CGG TTG ATG GAG

AAC AAC ATG ... 3';

(2) sequences having at least about 78.3% homology to said promoter sequence, preferably over about a 322 base pair overlap;

(3) functional promoter sequences comprised within the *Bradyrhizobium japonicum* nifH regulatory region as follows:

5' ... TTT GGC TGT TGG CGT TCA TGT TTG CGA TTG

TTT GTT CGT TGT CTG ACA GCC GGG CAG ATC TTG

TCA GAT CCA AAA CAG CCT ACG ATC GCG CGC CGG

CTG GTT GCT TTT GGA AAC GTA ATC AGA AGC TTA

AGG TGC CGG GTT AGA CCT TGG CAC GGC TGT

TGC TGA TAA GCG GCA GCA ACA CTG AGT GAG

GGC TGA GTG CAC GCC GAC GTG TAA GGC GAG

CGA TGC GCT CCT TCC CTT GAA CCC GTG TGC

CCC CGT TTC TGC GAG GGA AGC AAA GCT CGC

AAA AGA AGC GCG CAA CGT TTG GCA AAT CGG

TTG ATG GAG AGC AGC ... 3';

(4) sequences having at least about 78.3% homology to said promoter sequence, preferably over about a 322 base pair overlap.

Plasmids and bacterial strains comprising such DNA molecules are also provided. Said molecules may be comprised within the Sym plasmids of rhizobial bacteria or within other plasmids known to the art, or such molecules may be comprised within the chromosomes of the bacterial strains.

The foreign structural gene can be any structural gene known to the art, and preferably is a bacterial toxin gene of *Bacillus thurinoiensis*.

Methods for expressing such foreign structural genes under control of one of the above promoters are also provided, comprising the following steps:

(a) introducing a DNA molecule comprising a foreign structural gene under control of said promoter into a rhizobial strain capable of forming nodules on a plant, preferably soybean or siratro; and (b) infecting a plant with said rhizobial strain wherein nodules are formed and expression of mRNA or protein coded by said foreign structural gene occurs within said nodules. Plants capable of being infected by particular strains of rhizobia may be readily chosen by those skilled in the art.

For the sake of convenience and clarity, the following definitions are presented below:

(a) Promoter: the nucleotide sequence upstream from the transcriptional start site containing all the regulatory regions required for transcription.

(b) Regulatory region: DNA sequence(s) necessary but not necessarily sufficient to turn on expression of a gene. A gene is "under control of" a regulatory region when said sequences operate to determine whether the gene is active or inactive.

(c) Translational start site: the ATG codon translated into a methionine residue at the amino terminus of an open reading frame.

(d) Transcription start site: the first deoxynucleotide to be transcribed into an RNA sequence of an mRNA sequence.

(e) Foreign gene(s): (a) structural gene(s) isolated from an extraneous source organism.

(f) Vector: a means, such as a plasmid, for transferring genetic material into a host organism with a single replication origin which carries and replicates one or more fragments of foreign DNA.

(g) Foreign DNA: a fragment of DNA isolated from an extraneous source organism, i.e. an organism other than the host organism.

(h) Stringent hybridization conditions: incubation at 50° C. for 3 hours.

(i) Homology: identity of nucleotide sequences. "Percent homology" refers to the number of identical nucleotide sequences in a given number of overlapping base pairs. A "base pair overlap" is simply a specified number of contiguous base pairs of two different sequences lined up together so that each base pair of one sequence can be checked for identity with the corresponding base pair of the other sequence. When no number of overlapping base pairs is given, the total number of base pairs in the sequence to which the "homologous" sequence is being compared is to be understood.

(j) Transforming: refers to the transfer of foreign DNA to a host organism so as to enable expression of the foreign DNA in the host organism. A "transformed" organism is one which is distinguishable from a naturally-occurring organism because of the presence of the foreign DNA.

(k) Recombinant DNA molecule: a DNA molecule prepared by human intervention. It may be a piece of a larger DNA molecule such as a plasmid or a genome, or it may comprise several such pieces ligated together. A composite gene, which comprises a structural gene in combination with a promoter with which it is not found in nature, is an example of a recombinant DNA molecule.

DETAILED DESCRIPTION OF THE PREFERRED EMBODIMENTS

Table 1 provides the nucleotide and amino acid sequence of the gene and promoter region of Bradyrhizobium sp. (Parasponia).

Table 2 provides the nucleotide and amino acid sequence of the nifH gene and promoter region of *Bradyrhizobium japonicum*.

The invention is based in part on the isolation and characterization of the regulatory regions controlling the nitrogen fixation (nif) genes of Bradyrhizobium strains. A regulatory region can be combined with a structural gene isolated from an extraneous source organism ("foreign gene" herein) and combined in a plasmid to provide a novel plasmid bearing the foreign gene expressible under control of the nif gene regulatory region, and to provide a novel microorganism transformed by the novel plasmid. Alternatively, the composite gene, including the foreign structural gene and nif gene regulatory region, can be integrated with the chromosome of a host bacterial strain in order to maximize the stability of the trait conferred by the composite gene. Furthermore, a novel rhizobial strain can be constructed in which a nif regulatory region together with the structural gene or genes it normally controls is integrated with the host chromosome to enhance stability of the ability of fix nitrogen.

The novel plasmids disclosed herein are useful for amplifying the quantities of composite genes, for transferring such genes to selected bacterial hosts, for generating new host bacterial strains and as intermediates for the construction of other plasmids having one or more of the foregoing uses. The bacterial strains of the present invention are useful for expressing the composite gene, under certain conditions, to provide a useful product, to confer an advantageous property to a plant or to improve the rate, quality or efficiency of the nitrogen fixation process.

In particular, the properties of the novel strains are manifested within root nodules formed by novel rhizobial strains of the invention in symbiotic combination with a host plant. Depending upon the gene chosen for expression in the nodule, the nodule then serves as a production source for a protein coded by the gene. Examples of proteins which can be expressed in root nodules include the insect-toxic protein of *Bacillus thuringiensis* (Wong, H. C. et al. (1983) J. Biol. Chem. 258:1960), the hydrogenase found in some but not all rhizobial strains (Cantrell et al. (1983) Proc. Nat. Acad. Sci. USA 80:181), metallothionein (Karin, M. and Richards, R. I. (1982) Nucl. Acids Res. 10:3165), and prolactin (Cooke, N. et al. (1981) J. Biol. Chem. 256:4007–4016). The foregoing list is not intended as limiting, but merely as exemplary of the broad range of possibilities for synthesis of proteins in root and stem nodules of plants. In general the invention makes it possible to produce any protein that may be of use, either as a product extracted from the nodule, as an excretion product of the nodule, conferring an advantage for the host plant, or as a functional protein within the nodule itself, improving the effectiveness of the symbiotic interaction. In addition to the proteins disclosed herein, others will be apparent to those of ordinary skill in the art, taking advantage of the known or subsequently discovered properties of root nodules and of specific proteins.

A major advantage conferred by gene expression under control of a nif regulatory region in root nodules is derived from the inventors' recognition that such expression is regulated in a similar manner as the expression of the nif genes themselves. The foreign gene is only minimally expressed, if at all, in the free-living bacteria. However, the gene is maximally expressed within the root nodule. Furthermore, because of the specific nature of the host-bacterium symbiosis, gene expression occurs only in the selected plant species recognized by the modified bacterial strain. These properties consequently ensure, first, that the foreign gene expression provides maximum local effect of the expression product, and second, that environmental side effects are limited since gene expression can be confined to the nodular tissues of the selected crop or plant variety.

Despite the fact that many structural genes of rhizobial nif regions hybridize with previously isolated nif gene segments, as described supra, some rhizobial nif regions do not hybridize, as shown by Scott et al. supra. Furthermore, most of the regulatory regions so far identified are substantially different from one another. In fact, as discovered in the course of the experiments leading to the present invention, the organization of the nifH, D and K genes differs among rhizobial species in a manner difficult to generalize at present. Many species have single regulatory regions apparently controlling the H, D and K genes. However, as disclosed herein, Bradyrhizobium sp. (Parasponia) has a separate, distinctive region regulating expression of nifH, and this gene maps at a different genetic locus from nifD or K. The techniques disclosed herein provide the first systematic means for isolating and genetically manipulating such regulatory regions for useful purposes.

In the present invention, nifH genes of slow-growing, broad host range Bradyrhizobium sp. (Parasponia) strain ANU289 have been isolated and partly sequenced. In contrast to previously studied nitrogen fixing prokaryotes, the nifH and nifD genes are unlinked in Bradyrhizobium sp. (Parasponia).

Cloned DNA fragments of the nifH, nifD and nifK genes of the free living organism *Klebsiella pneumoniae* were used to identify and isolate the corresponding symbiotic genes of Bradyrhizobium sp. (Parasponia) strain ANU289. These three genes (nifH, nifD, and nifK) constitute the nitrogenase complex. They may all be closely linked or they may be unlinked. In particular, a recombinant plasmid (pKnif-2) carrying K. pneumoniae DNA and coding for the entire nifH gene and the N-terminal 207 amino acids of nifD gene has been cloned and used as a hybridization probe.

To isolate the nitrogenase complex structural genes from Bradyrhizobium sp. (Parasponia), a gene bank of strain ANU289 DNA was constructed by partial cleavage of genomic DNA with Sau3A and ligation into BamHI-cleaved DNA isolated from the phage vector lambda-Charon 28. The construction of genomic libraries in the bacteriophage vector lambda-Charon 28 (Liu, C. P. et al. (1980) Science 209:1348-1353), and procedures for screening libraries have been described (Scott, K. F. et al. (1982) J. Mol. Appl. Genet. 1:315-326). Cloned DNA pKnif2 fragments $^{32}$p labelled, of the nif genes of *Klebsiella pneumoniae* were used to probe for nitrogenase complex genes of Bradyrhizobium sp. (Parasponia) It was discovered that several positivelyhybridizing recombinants could be obtained. The restriction map of this phage clone was shown to be identical to that of the corresponding region in the Bradyrhizobium sp. (Parasponia) genome. This was determined by hybridization of $^{32}$p-labeled subfragments of lambdaPR289nif-1 to restriction digests of ANU289 DNA. A 4.5 kilobase PstI fragment homologous to the K. pneumoniae nifH-specific probe was subcloned into the plasmid vector pBR32 and the resultant recombinant clone (pBR289nif-2) was extensively mapped by restriction endonuclease analysis. This clone was used as a template for the direct sequence analysis of the nifH gene.

The entire sequence of the Bradyrhizobium sp. (Parasponia) DNA including its nifH coding region and associated regulatory region has been determined (Table 1). There is a translation initiation codon 572 base pairs (bp) from the PstI site at the 5' end of the sequence followed by an open reading frame of 882 bp. The amino acid sequence predicted from the nucleotide sequence of this reading frame is homologous to that of all other nifH genes so far determined. The N-terminal methionine of this nifH gene is preceded by a purine-rich region (t'GGAG-3') which is identified as a ribosome binding site for the initiation of translation.

The 5'-end of the nifH mRNA transcript was mapped by an S1-nuclease procedure (Sharp, P. A., Berk, A. J. and S. M. Berget (1980) in *Methods of Enzymol.* 65, (L. Grossman and K. Moldave, eds.) New York, Academic Press, pp. 750-758) using polyA-RNA isolated from Siratro (*Macroptilium atropurpureum*) nodules inoculated with ANU289. The nifH coding sequence is preceded by a long leader sequence of 155 bp. On the basis of the S1-mapping analysis, presumptive RNA polymerase recognition sequences are assigned. It is clear that the sequences in the −10 region (5'-ATTGCT-3') and −35 region (5'-TAAGCG-3') of the gene are not homologous to the consensus RNA polymerase recognition sequences preceding E. coli operons (TATAAT and TTGACA, respectively) (Siebenlist, U. et al. (1980) Cell 15 20:269-281). More significantly the promoter sequences share very little homology with those assigned for the Anabaena transcript (Haselkorn, R. et al. (1982) in *Cyanobacteria: Cell Differentiation and Function* G. C. Papageorgiou, L. Packer, eds.). Significantly the primary sequences of the regulatory regions between most different nitrogen fixing organisms vary fundamentally. These differences are related to the specificity of the interaction between a plant species and a nitrogen fixing bacterial species.

In all nitrogen-fixing species examined previously the nifH gene is immediately followed by the gene coding for the α-subunit of the Mo-Fe protein, i.e., the nifD gene. The N-terminal sequences of the nifD gene from K. pneumoniae (Scott, K. F. et al. (1981) J. Mol. Appl. Genet. 1:71-81), R. trifolii (supra) and R. meliloti (Torok, I. and Kondorosi, A. (1981) Nucleic Acids Res. 9:5711-5723) have been determined and the predicted protein sequences encoded by these nifD genes are conserved. Surprisingly, however, in Bradyrhizobium sp. (Parasponia) ANU289, no sequence analogous to the Klebsiella or Rhizobium nifD genes can be found in the 591 bp following the nifH gene. It has now been shown that the nifH gene is separated by at least 13 kilobases from the nifD gene. Hybridization analysis of the phage clone lambdaPR289nif-1 DNA with a fragment of K. pneumoniae DNA encoding nifD specific sequences showed that there were no sequences homologous to the K. pneumoniae nifD probe on the 13 kb of DNA following nifH. This unexpected finding was confirmed by the isolation of clones carrying nifD specific sequences from the genomic library and hybridization analysis of these clones with nifH specific sequences. Such an analysis demonstrates that nifH is not encoded on these cloned fragments. Clearly, the nifH and nifD genes are not encoded in the same operon in Bradyrhizobium sp. (Parasponia) ANU289. Furthermore, as disclosed herein, the nifK gene encoding the remaining component of the nitrogenase enzyme complex (α-subunit of the Mo-Fe protein) has been mapped by hybridization analysis to be immediately to the 3'-side of nifD.

Sequence analysis was carried out by the chemical method (Maxam, A. M. and W. Gilbert (1980) Methods in Enzymology 65:499-560) from defined restriction sites and by a method based on the generation of a series of deletions with the double stranded exonuclease Bal31 (Legerski, R. J. et al. (1978) Nucleic Acids Res. 5:1445-1464) followed by subsequent cloning of these deleted fragments into the phage vector M13mp (Vieira, J. and J. Messing (1982) Gene 19:259-268) and sequence analysis by the chain termination method (Sanger, F. et al. (1977) Proc. Nat. Acad. Sci. U.S.A. 74:5463-5467).

*Bradyrhizobium japonicum* (formerly called *Rhizobium japonicum*), a member of the slow-growing group of rhizobia or "bradyrhizobia" (Jordan, D. C. (1982) Int. J. Syst. Bacteriol. 32:136-139) is an important soybean symbiont and is therefore most important in the agricultural industry. The structural organization of the nif genes differs from "fast-growing" Rhizobia in that the nifH and nifDK genes which code for the polypeptides of the nitrogenase complex, have been shown to be unlinked (Kaluza, K. et al. (1983) J. Bacteriol. 155:915-918). The interesting question was raised as to whether or not the expression of nitrogen fixation genes was coordinately regulated and whether there were homologies in the DNA control regions. The three nitrogenase structural genes have previously been cloned (Hennecke, H. (1981) Nature (London) 291:354-355). The polypeptides of dinitrogenase were expressed in E. coli (Fuhrmann, M. and H. Hennecke (1982) Mol. Gen. Genet. 187:419-425); the nifD gene product (α-subunit) was shown to possess a molecular weight of 58,000, whereas the nifK gene product (β-subunit) has a molecular weight of 55,000. The nifD and nifK genes are organized on a transcriptional unit, and are transcribed in the direction nifDK. Interestingly, no other nif genes were found in the immediate vicinity on either side of nifDK. The sources of DNA were the B. japonicum nifDK-containing recombinant plasmid pRJ676 and subclones thereof (Hennecke, H. (1981) supra) and the nifH containing recombinant plasmid pRJ7000 and subclones thereof. Polypeptides encoded by these various B. japonicum recombinant plasmids were analyzed using the polypeptide products synthesized in mini cells of E. coli. DNA sequencing analysis was done using both the chemical method (Maxam, A. M. and W. Gilbert (1980) Methods Enzymol. 65:449-561) and the chain termination method (Sanger, F. et al. (1977) Proc. Nat. Acad. Sci. U.S.A. 74:5463-5467). All restriction endonuclease sites relative to B. japonicum were confirmed by overlapped sequencing. Both DNA strands of the genes and flanking sequences were sequenced. Transcriptional start points and the extent of the mRNA transcripts were determined by nuclease S1 mapping (Berk, A. J. and P. A. Sharp (1977) Cell 12:721-732).

Figure 1:
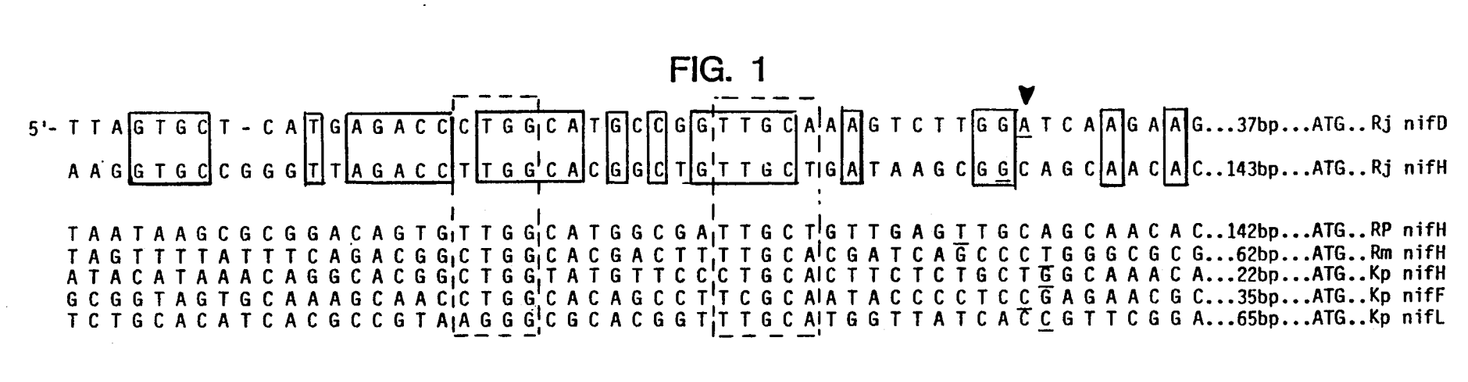
FIG. 1 shows a comparison of the 5' regions showing the transcriptional and translational start sites for *Bradyrhizobium japonicum* nifD, B. japonicum nifH, Bradyrhizobium sp. (Parasponia) nifH, R. meliloti nifH, and K. pneumoniae nifH, F and L.
Figure 2:
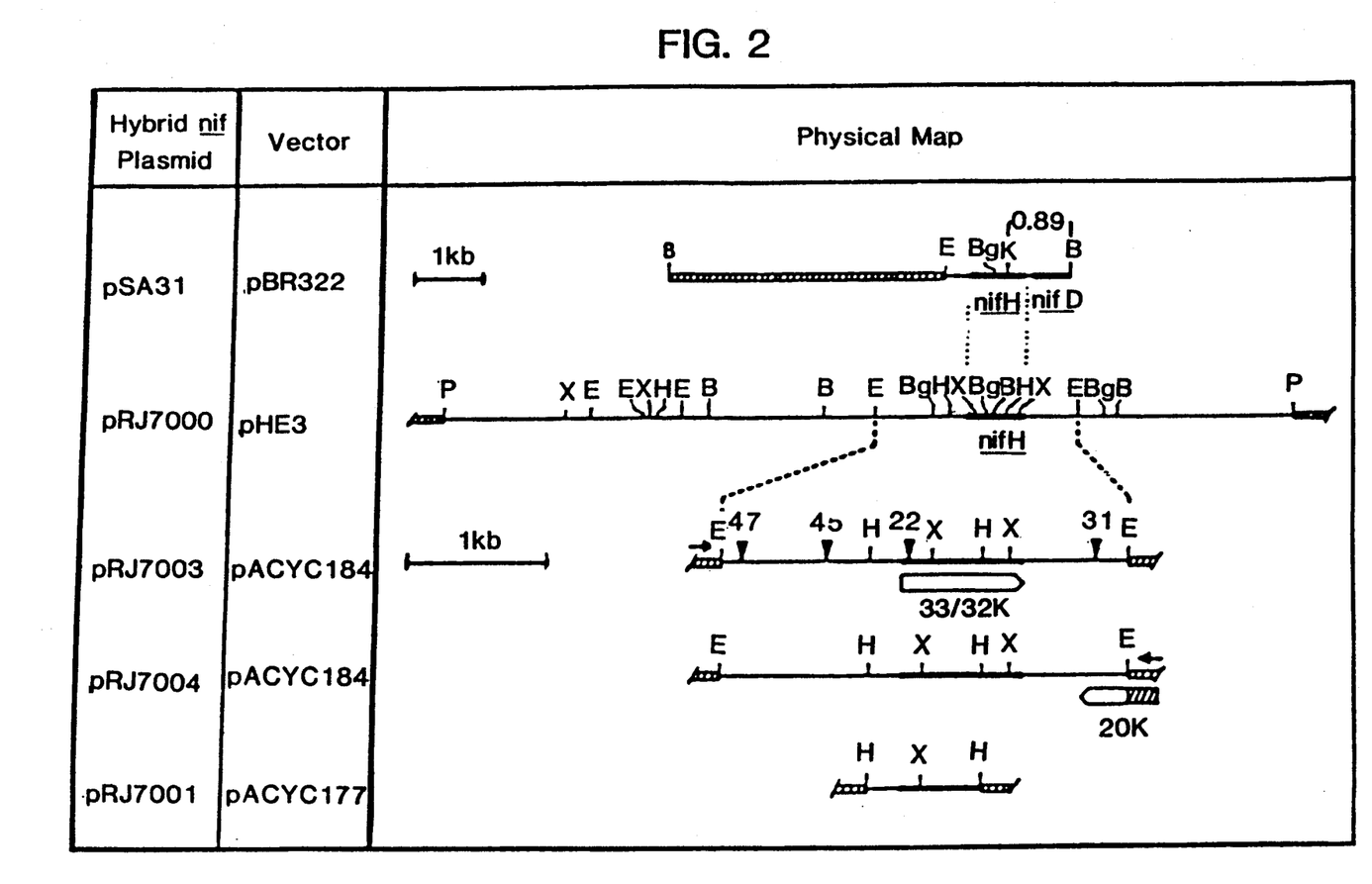
FIG. 2 shows the B. japonicum nifH fragments incorporated into various hybrid nif plasmids.

Seven base pairs (bp) upstream from the ATG translation start site of the B. japonicum nifD gene there is a 5'-AGGA-3' sequence marking a perfect ribosome binding site (Shine J. and L. Dalgarno (1974) Proc. Nat. Acad. Sci. U.S.A. 71:1342-1346; Stormo, G. D. et al. (1982) Nucleic Acids Res. 10:2871-2996). A similar sequence 5'-TGGA-3 occurs eight bp upstream from the ATG translation start site of the nifH operon (Table 2).

The utilization of the triplet codons of the B. japonicum nifD gene shows that two codons are not used. Most of the other codons are used in an asymmetric or strongly asymmetric manner (e.g., those for Phe, Asn, Gly and Cys). The codon usage for the sequenced 622 bp stretch of *Klebsiella pneumoniae* nifD DNA (Scott, K. F. et al. (1981) J. Mol. Appl. Genet. 1:71-81) is substantially different. In the case of B. japonicum, when more than two triplets are available for a given amino acid, there is a preference of using those with a G and/or C in the "wobble" position. This could reflect the G+C content of slow-growing rhizobial species.

The complete nucleotide sequence of the B. japonicum nifH gene is presented (Table 2) together with the predicted amino acid sequence of the nifH gene product (the dinitrogenase reductase). From the presumptive start codon (ATG) to the stop codon (TAA) there is an open reading frame of 882 nucleotides corresponding to 29 amino acids. Eight nucleotides upstream from the start codon there is a ribosome binding site, 5'-TGGA-3'.

The transcriptional start point of the B. japonicum nifH gene was determined as described supra. RNA both from free-living, N₂-fixing B. japonicum cells and from soybean root nodule bacteroides was hybridized to a ³²P-labelled HindIII/HinfI fragment which extends from position −201 of the 5'-nifH flanking region to nucleotide +41 of the coding region (see Table 2). The hybrid was digested with nuclease S1, and the protected DNA was electrophoresed adjacent to a Maxam-Gilbert "sequencing ladder" of the same HindIII/HinfI fragment. The transcription start point was thus determined to be the G located 153 nucleotides upstream from the beginning of the nifH coding region. The transcription start point is immediately preceded by the promoter region (for definition, see above) containing the sequence 5'-TTGG-8bp-TTGCT-3'. (Note: the corresponding sequence of the nifDK promoter given above is 5'-CTGG-8bp-TTGCA-3'.) Furthermore, the region from positions −185 to −160 (Table 2) contains 19 nucleotides found at identical positions in the promoter region of the

The region flanking the 3'-end of the B. japonicum nifH coding region was also examined for termination signals. A very obvious inverted repeat structure was found 13 nucleotides downstream from the last nifH codon (Table 2). Messenger RNA transcribed from this region could potentially form a characteristic stem and loop structure:

The stem is formed by 11 consecutive base pairs of which eight are G-C pairs. This structure is quite stable with a free energy of DeltaG° (25° C.)=−26.2 kcal estimated according to Tinoco et al. (Tinoco, J., Jr. et al. Nature New Biology 246:40-41). On the 3'-flanking side the inverted repeat structure is followed by a C-rich region.

The postulated G/C-rich terminator region is of the "E. coli" type, except that the stem and loop structure is followed by a C-rich region rather than a T-rich region (Rosenberg, M. and D. Court (1979) Ann. Rev. Genet. 13:319-353). The postulated ribosome binding site is also similar to those of E. coli genes (Shine, J. and L. Dalgarno (1974) Proc. Nat. Acad. Sci. U.S.A. 71:1342-1346) which may explain why it has been possible to translate nifH fusion mRNA into (a) nifH-specific polypeptide(s) in E. coli minicells. These translation experiments have revealed a protein doublet with molecular weights of 33,000 and 32,000 encoded by the same DNA region. At present it is unknown whether this reflects protein processing or the presence of two overlapping open reading frames. Indeed, 12 bp upstream from the nifH coding region, and in frame with it, there is a second possible ATG initiator codon, but this second codon is not preceded by a characteristic Shine-Dalgarno sequence (Table 2). It is interesting to note that a similar doublet of the K. pneumoniae dinitrogenase reductase was found in vivo (Roberts, G. P. et al. (1978) J. Bacteriol. 136:267-2179), and that the expression of the R. meliloti nifH gene has also led to the synthesis of two proteins with similar molecular weights (Weber, G. and A. Puhler (1982) Plant. Molec. Biol. 1:305-320).

A portion of the nifH promoter sequence of B. japonicum differs from the nifDK promoter region in only a few base pairs. Both promoter sequences contain a characteristic region between nucleotide 9 and 25 upstream from the transcription start site with some similar features of the K. pneumoniae nif promoters (Beynon, J. et al. (1983) Cell 34:665-671). However, with respect to the nifH and nifDK promoters of B. japonicum there are nine additional identical nucleotides (5'-GTGC-5bp-AGACC-3') immediately preceding (i.e., upstream) these sequences. These sequences (i.e., 5'-GTGC-5bp-AGACC-3') could be involved in the correct functioning of the promoters. As some of these elements are likely to be involved in nif gene regulation, it is surprising to observe what may be remnants of nif gene control circuits in the non-symbiotic K. pneumoniae which appear to operate in the agriculturally important symbiotic B. japonicum. When DNA sequences are compared, then, in addition to the similarities with the promoter elements of Klebsiella pneumoniae (Sundaresan, V. et al. (1983) Nature (London) 301:728-732; Beynon, J. et al. (1983) Cell 34:665-671; Ow, D. W. et al. (1983) Proc. Nat. Acad. Sci. U.S.A. 80:2524-2528), the nifH and nifDK promoters of B. japonicum have some homology with the nifH promoter (Pl) from Rhizobium meliloti (Sundaresan, V. et al. (1983) Nature (London) 301:728-732; Better, M. et al. (1983) Cell 35:479-485). However, it should be noted that the regions of nonhomology are likely to be most significant because the species which can be infected by B. japonicum are quite different from those species which can be infected by Rhizobium meliloti.

Since the promoter regions of the nifH operons of B. japonicum and Bradyrhizobium sp. (Parasponia) have been isolated, characterized and cloned, it is possible to delete the nifH nitrogenase gene, i.e., the DNA sequence normally transcribed into mRNA or RNA, and replace it with (a) structural gene(s) isolated from an extraneous source organism ("foreign gene" herein). The foreign gene(s) thus placed under the control of the nifH promoter can then be inserted into a plasmid vector followed by conjugation into a rhizobial organism, preferably B. japonicum or Bradyrhizobium sp. (Parasponia). The foreign gene is then expressed in this novel organism under conditions where the nif gene promoters are activated. Alternatively, the novel composite gene which includes the foreign structural gene and the nif gene promoter, can be integrated with the chromosome of a host rhizobial organism under conditions where the nif gene promoters are activated. Alternatively, the novel composite gene which includes the foreign structural gene and the nif gene promoter, can be integrated with the chromosome of a host rhizobial organism in order to maximize the stability of the trait conferred by the composite gene.

A principal feature of the present invention is the construction of a plasmid having an inserted foreign gene under control of a nifH promoter. The structural gene must be inserted in the correct position and orientation with respect to the promoter in order to obtain expression of the structural gene controlled by the promoter. Position has two aspects. The first relates to on which side of the promoter the structural gene is inserted. It is known that the majority of promoters control initiation of transcription and translation in one direction only along the DNA. The region of DNA lying under promoter control is said to lie "downstream" or alternatively on the 3'-side of the promoter. Therefore, to be controlled by the promoter, the correct position of the foreign gene insertion must be "downstream" from the promoter. The second aspect of position refers to the distance, in base pairs, between functional elements of the promoter, for example, the transcription initiation site and the translational start site of the foreign gene.

Substantial variation appears to exist between promoters with respect to this distance. Therefore the structural requirements in this regard are best described in functional terms. Optimum spacing can be achieved by experiments varying the length of this distance. As a first approximation, reasonable operability can be obtained when the distance between the promoter and the inserted foreign gene is similar to the distance between the promoter and the gene it normally controls. Orientation refers to the directionality of the structural gene. By convention, that portion of a structural gene which ultimately codes for the amino terminus of a protein is termed the 5' end of the structural gene, while that end which codes for amino acids near the carboxyl end of a protein is termed the 3' end of the structural gene. Correct orientation of a structural gene is with the 5' end thereof proximal to the promoter. An additional requirement in the case of constructions leading to fusion protein expression is that the insertion of the structural gene into an existing nitrogenase complex structural gene sequence must be such that the coding sequences of the two genes are in the same reading frame phase, a structural requirement which is well understood in the art.

In order to express foreign genes in the 3'-side of the nitrogenase complex regulatory sequences, it is first advantageous to construct a double-stranded DNA sequence corresponding to the nifH regulatory sequences. To achieve this, synthetic DNA primer complementary to the ribosome binding site of the mRNA and extending a few nucleotides to the side thereof is first constructed. Then the cloned nifH fragment is excised from the vector, purified and the excised nifH fragments are ligated into appropriate single stranded DNA phage (e.g., fd) vectors. The resultant recombinant DNA plasmids are then transformed into E. coli strains, and single colonies are propagated. Those colonies which extrude single stranded templates corresponding to the mRNA strand are isolated. The synthetic DNA is used as a primer on these single stranded templates to generate double stranded DNA by primer extension with DNA polymerase I (Klenow fragment). This double stranded DNA will extend from the ribosome binding site to an indeterminate point within the single stranded DNA vector. Any single stranded regions are removed by S1 nuclease treatment. Alternatively, a double stranded vector, e.g., pBR322, may be denatured and replicated using the same synthetic DNA primer. If a double stranded vector is used, then suitable precautions well known to those skilled in the art should be used to avoid the presence of background unlabelled fragments, e.g., it is possible to demonstrate the presence of contaminating fragments by use of restriction maps.

Then synthetic EcoRI linkers are ligated to the DNA fragments followed by digestion with EcoRI and that restriction endonuclease (termed endonuclease A for generality) which recognizes the restriction site at the 5' end of the nifH. The resultant DNA fragments are then cloned into an EcoRI-endonuclease A cleaved plasmid, transformed into a suitable E. coli host and amplified. The choice of plasmid is based on principles of operating convenience and location of the appropriate restriction sites, as will be understood by those of ordinary skill in the art.

Following amplification, isolation and repurification, this same plasmid is then cleaved with endonuclease A and treated with S1 nuclease or BAL-31 for a short time to produce blunt ended fragments. The plasmid is now cleaved with EcoRI and the fragment is cloned into the wide host range plasmid pRK290 to produce a pRK290-nif regulatory fragment construct. Alternatively, another wide host range plasmid, pSUP204, can be used to construct the recombinant nif regulatory plasmid.

Alternatively, the DNA fragments provided with EcoRI-endonuclease A-specific ends are initially cloned into a mobilizable broad host range vector capable of replication in either E. coli or most other gram-negative bacteria, such as pSUP104 or pSUP204 (Puhler, A., Simon, R. and U. Priefer "Class II Mobilizable Gram-Negative Plasmid," U.S. patent application Ser. No. 510,334, filed June 30, 1983,now U.S. Pat. No. 4,680,264). After amplification, the recombinant plasmid is transferred directly to the desired recipient strain.

In order to clone and express foreign genes, appropriate DNA fragments carrying these foreign genes are isolated and synthetic EcoRI linkers are ligated to the fragments (EcoRI-foreign gene-EcoRI). The EcoRI-foreign gene-EcoRI DNA fragments are then ligated into EcoRI-cleaved vector DNA, for example, pSUP104 or pSUP204, resulting in a nif-regulated expression plasmid, pSS104 or pSS204, respectively, and transformed into *Escherichia coli*. After selection and amplification, the nif-regulated expression plasmid is then transferred with the aid of helper plasmids to the appropriate rhizobial or Agrobacterium strain by mating.

The exconjugant rhizobial strains are then used to infect soybean plants or other appropriate legumes which are subsequently assayed for the production of foreign mRNA and/or protein.

Plasmids are lost rather easily from bacterial strains, thus leading to the loss of expression of those genes carried on the plasmids. One method of stabilizing the expression of certain genes carried on plasmids, or, for that matter, any foreign DNA segment, would be the introduction of such genes or foreign DNA segments, hereinafter termed "introduced DNA," into the chromosome of the host bacteria. Such a system employs a "suicide vector" and, preferably, a transposon.

Suicide vectors are plasmid molecules which replicate stably in one bacterial host (in this case, *Escherichia coli*) but fail to replicate in a different bacterial species (e.g., *Rhizobium trifolii*).

Transposons are genetic elements which are able to move (translocate) from one location to another in DNA. The translocation process is mediated by gene products encoded on the transposon and is dependent upon the integrity of repeated sequences (directly or indirectly repeated) located at each end of the transposon. Transposons generally carry a gene (or genes) encoding resistance to one (or more) antibiotics. The transposon and the suicide vector are linearized and relegated into a single recombinant DNA molecule.

The general method of transferring introduced DNA segments to the chromosome of a gram-negative bacterial strain other than E. coli is outlined here. The DNA fragments to be introduced can be generated in a number of ways: (a) by restriction with site-specific restriction endonucleases; (b) by partial or complete digestion with restriction endonucleases which generate DNA fragments having blunt ends; (c) by digestion of DNA with the enzyme DNAse I in the presence of $Mn^{++}$ ions thus generating random fragments which are generally blunt-ended; or (d) by shearing the DNA into large fragments.

In the preferred method, the suicide vector carrying a transposon with an antibiotic resistance gene is linearized and the appropriate fragment of introduced DNA is ligated into a "co-integrated recombinant molecule." The fragment of DNA is inserted into a restriction endonuclease site within the transposon in such a manner that the insertion does not disrupt normal transposition nor expression of the drug resistance marker. This ligated DNA is then transformed in an E. coli strain in which it can be amplified and mobilized for transfer into other gram-negative bacteria.

The cloned, introduced DNA fragment from this E. coli strain can then be moved into the chromosome of any gram-negative bacterium, e.g., *Bradyrhizobium japonicum*. This is most conveniently achieved by the process of bacterial conjugation. The E. coli strain carrying the suicide vector which contains an antibiotic resistance gene is mixed with cells of the antibiotic sensitive gram-negative strain on the surface of a nutrient agar plate. The plate is incubated for a period (4–16 hours) at the optimum temperature of the gram-negative strain and, during this time, cells of each bacterial species come into physical contact (conjugation) and the suicide vector is transferred from the donor E. coli to the recipient gram-negative strain. The cell mixture is washed off the plate and spread on an agar plate which is selective for the antibiotic resistance. It is preferred to include selection means that select against growth of the E. coli parent strain once the conjugation and transfer is completed.

Since the suicide vector containing the introduced fragment of DNA cannot be amplified autonomously in the recipient gram-negative strain, a transfer of genetic material to the bacterial chromosome can occur in one of three ways: (a) If a fragment of the recipient gram-negative bacterial chromosome (BC) has been previously inserted into the suicide vector (SV) thus creating a region of homology between the suicide vector and the recipient gram-negative bacterial chromosome, then a single reciprocal recombination will result in the incorporation or cointegration of the entire recombinant molecule into the chromosome of the recipient gram-negative bacterial chromosome. (b) If a fragment of the recipient gram-negative bacterial chromosome has been previously inserted into the suicide vector thus creating a region of homology between the suicide vector and the recipient gram-negative bacterial chromosome and then an introduced DNA fragment and a drug resistance gene are inserted into this region of homology, a double reciprocal recombination event will incorporate only the introduced DNA fragment and the drug resistance gene into the chromosome of the recipient gram-negative bacterial strain. Such recombination is sites-pecific, the chromosomal location being determined by the fragment of chromosomal DNA carried on the suicide vector. (c) In the preferred method, the transposon containing an introduced DNA fragment and an antibiotic resistance gene may be transposed into the bacterial chromosome of the recipient gram-negative bacterial strain. In addition, Tn refers to a transposon used to transpose the inserted DNA into the bacterial chromosome. Selection for the antibiotic resistance ensures maintenance of the inserted DNA.

EXAMPLES

Isolation of DNA:

Genomic DNA was isolated from individual bacterial colonies as previously described (Scott, K. F. et al. (1981) J. Mol. Appl. Genet. 1:71-81). Extraction of DNA from liquid cultures was done by the same procedure except that the cell pellet from 5 ml culture was resuspended in 1 ml 25% sucrose in TE (10 mM Tris-HCl pH 8.0 1 mM EDTA) and incubated for 30 minutes at room temperature with lysozyme (1 mg/ml) and EDTA (50 mM). The suspension was diluted to 20 ml with TE and cells were lysed by the addition of SDS (to 0.4% w/v) and Pronase (100 µg/ml) with incubation at 37° C. for two hours. The lysate was extracted twice with phenol/chloroform (equal volume 1:1) and dialysed against two changes of 0.3M NaCl in TE. DNA was precipitated with 2.5 volumes of ethanol at −20.C.

For isolation of plasmid DNA, cultures were grown in L-broth and amplified by the addition of spectinomycin (250 µg/ml). Plasmid DNA was isolated by a polyoxyethylene ether-deoxycholate lysis procedure (Watson, J. et al. (1980) Plasmid 4:175-183). Cells from one liter cultures were harvested by centrifugation and resuspended in 10 ml cold 25% (w/v) sucrose in TE. After addition of lysozyme (3 mg/ml) and EDTA (200 mM), the cells were lysed by the rapid addition of 15 ml 1% (v/v) polyoxyethylene ether 58, 0.4% (w/v) sodium deoxycholate in TE and incubation at 4° C. for 10-20 minutes. The lysate was centrifuged at 17,000 rpm for 40 minutes to pellet cellular debris. DNA was precipitated from the supernatant by the addition of 3% (w/v) NaCl and ¼ volume 50% (w/v) polyethylene glycol 6000 with incubation on ice for at least 2 hours. After centrifugation at 5000 rpm for two minutes, the DNA pellet was resuspended in 5 ml 50 mM NaCl in TE before addition of 8 g cesium chloride and 0.6 ml ethidium bromide (10 mg/ml) and incubation on ice for 30 minutes. Excess polyethylene glycol was removed by centrifugation at 10,000 rpm at 4° C. for 30 minutes. The density of the supernatant was adjusted to 1.59-1.61 g/ml by the addition of 1.5 ml 50 mM NaCl in TE. plasmid DNA was banded by centriguation at 100,000 g for 40 hours at 18° C.

Molecular cloning and hybridization procedures

The construction of genomic libraries in the bacteriophage vector lambda-Charon 28 (Liu, C. P. et al. (1980) Science 209:1348-1353) and procedures used for screening libraries have been described previously (Scott, K. F. et al. (1982) J. Mol. Appl. Genet. 1:315-326).

Hybridization probes were prepared by primed synthesis with DNA polymerase I (Klenow fragment) using denatured random calf thymus DNA primers. Linearized plasmid DNA (100 mg) was heat-denatured by boiling for 2 minutes with 100 µg random primers (8-12 nucleotide fraction of DNAse I-treated calf thymus DNA) in 20 µl and cooled on ice for 30 seconds. Denatured DNA was incubated for 30 minutes at 37° C. with 1 unit DNA polymerase I (Klenow fragment) in 10 mM Tris-HCl pH 7.4, 8 mM $MgCl_2$, 10 mM β-mercaptoethanol, 600 µM each of dGTP, dATP, and dTTP and 30 µCi α-$^{32}$P-dCTP (>7000 Ci/mmol, Amersham). The reaction was stopped by phenol/chloroform extraction and the aqueous phase passed over a Sephadex G-50 column to remove unincorporated radioactivity. Peak fractions (specific activity $10^7$–$10^8$ cpm/µg DNA) were precipitated by the addition of E. coli to tRNA (20 µg) and 2.5 vol. ethanol at −20° C.

DNA was transferred from agarose gels and immobilized on nitrocellulose sheets by depurination, denaturation and blotting as described (Southern, E. M. (1975) J. Mol. Biol. 98:503-517).

Sequencing

Sequence data was obtained by the use of both the chemical cleavage method (Maxam, A. M. and Gilbert, W. (1980) in Methods in Enzymol., 65, L. Grossman and K. Moldave, eds. (New York, Academic Press, pp. 499-560) and the chain termination method (Sanger, F. et al. (1977) Proc. Nat. Acad. Sci. U.S.A. 74:5463-5467). For the latter procedure, template was generated by the construction of a series of defined deletions with the exonuclease Ba131 followed by cloning into the bacteriophage vector M13mp8 as follows. Plasmid DNA (5 µg) was linearized with the endonuclease XhoI, digested with Bal31 (20 units) in 20 mM Tris-HCl pH8.1, 12 mM $CaCl_2$, 600 mM NaCl and 1 mM EDTA at 31° C. Samples (10 µl) were taken at one minute time intervals and the digestion stopped by phenol-chloroform extraction and ethanol precipitation. The Bal31-digested DNA was then cleaved with EcoRI, ligated into EcoRI-HincII cleaved M13mp8 DNA and transformed into E. coli JM103 cells (Scott, K. F. et al. (1981) J. Mol. Appl. Genet. 1:71-81). Template DNA was isolated and sequenced.

Molecular cloning and DNA sequence of the nifH gene from Bradyrhizobium sp. (Parasponia)

Genomic DNA was isolated from Bradyrhizobium sp. (Parasponia) ANU289 and partially cleaved with the restriction endonuclease Sau3A. The resulting DNA fragments were ligated into BamHI cleaved Lambda-Charon 28 DNA and the phage DNA was packaged in vitro to generate an ANU289 library. This library was screened by hybridization with the 750 bp nifH specific fragment from pKnif-2 (Scott, K. F., et al. (1981) supra). DNA was prepared from the positively-hybridizing recombinant (PR289 nif-1) and cleaved with PstI. The resultant PstI restriction fragments were then ligated into PstI cleaved pBR322 and transformed into E. coli RR1. Recombinants were selected by hybridization to pKnif-2 sequences. DNA was prepared from the recombinant plasmid (pPR289-nif-2) and sequenced by chemical and chain termination methods. A PstI-BamHI fragment was obtained by cleaving pBR289-nif-2 with the restriction endonucleases PstI and BamHI and then purifying the fragment.

Source of DNA and DNA sequencing: Bradyrhizobium japonicum

For nifH, a previous Southern blot hybridization experiment with total DNA of *Bradyrhizobium japonicum* had revealed that a PstI fragment of about 12-14 kilobase pairs (kb) specifically hybridizes to radioactively labelled nifH DNA from *Klebsiella pneumoniae* and *Rhizobium meliloti*. In order to clone this fragment, size-fractionated jaconicum DNA (PstI fragments between 10 and 16 kb) was ligated with PstI-digested DNA of the cloning vector pHE3, and the recombinant DNA was transformed into E. coli RR28 (Hennecke, H. et al. (1982) Gene 19:231-234). As this cloning system enables the direct selection of recombinant plasmids, 730 transformants were picked and screened for the presence of the B. japonicum nifH gene by interspecies colony hybridization under stringent conditions. Stringent conditions are defined here as incubation at 50° C. for 3 hours. One colony (pRJ7000) contained the desired recombinant plasmid with a 12.1 kb insert that hybridized to both the ($^{32}$P)-labelled nifH-containing R. meliloti HindIII fragment of pRmR2 (Ruvkun, G. B. and F. M. Ausubel (1980) Proc. Nat. Acad. Sci. U.S.A. 77:191-195), and to the ($^{32}$P)-labelled nifH containing K. pneumoniae EcoRI/KpnI fragment of pSA31 (Scott, K. F. et al. (1981) J. Mol. Appl. Genet. 1:71-81).

Nucleotide sequence data were obtained using both the chemical method and the chain termination method. Chemical sequencing was done by the methods of Maxam and Gilbert (Maxam, A and W. Gilbert (1980) Methods Enzymol. 65:499-561) except that the A+G modifications procedure was done as described by Gray et al. (Gray, C. P. et al. (1978) Proc. Nat Acad. Sci. U.S.A. 75:50-53). For the chain termination method (Sanger, F. et al. (1977) Proc. Nat. Acad. Sci. U.S.A. 74:5463-5467), DNA fragments were subcloned into the bacteriophages M13mp7, -mp18, -mp9, -mp10 and -mp11 (Messing, J. (1983) Methods Enzymol. 101:20-78). After transformation of E. coli JM103, recombinant phages were screened using the dot-blot hybridization technique. Single stranded DNA was isolated as described (Messing, J. (1983) Methods Enzymol. 101:20-78) and annealed to primers purchased from Bethesda Research Laboratories (26 bases) or New England Biolabs (15 bases). All restriction sites were confirmed by overlapped sequencing, and the complete nifH (Table 2) region was sequenced on both strands of DNA. A computer program was used for analysis and storage of the sequence data (Larson, R. and J. Messing (1982) Nucleic Acids Res. 10:39-49).

Determination of promoter and terminator regions by S1 nuclease mapping: Bradyrhizobium japonicum The transcriptional start points of the B. japonicum nifH gene were determined by nuclease S1 mapping (Berk, A. J. and P. A. Sharp (1977) Cell 12:721-732) with modifications (Weaver, R. F. and C. Weissman (1979) Nucleic Acids Res. 7:1175-1192). RNA was extracted as described previously (Kaluza, K. and H. Hennecke (1981) Arch. Microbiol. 130:38-43). RNA from free-living, aerobic B. japonicum cultures served as a negative control. For nifH, a 5'-$^{32}$P-labelled HindIII/HinfI fragment extending from position −201 to +41 of the coding region was used (Table 2). After strand separation and hybridization to mRNA (45° C. for 12 hours) unhybridized nucleic acids were digested with nuclease S1 (Boehringer Mannheim), and the protected DNA was electrophoresed adjacent to a Maxam-Gilbert "sequencing ladder" of the same HindIII/HinfI fragment (nifH).

Expression of foreign genes under the control of a nif promoter DNA region. Method I Construct a synthetic DNA primer which is complementary to the ribosome binding site of the B. japonicum nifH gene (5'-GCTGCTCTCCATCAACCG-3'). A DNA fragment which spans the region from an EcoRI restriction site upstream (i.e., 5'- to the ATG translation initiation codon) to XhoII site downstream (i.e., 3'- to the ATG translation initiation codon) is then subcloned into a single stranded DNA phage, transformed into E. coli JM103 and propagated therein. The cloned fragment is amplified and single stranded templates (ca. 1 μg) are recovered from the supernatant following centrifugation of the bacterial host. A 10-fold excess of the synthetic DNA primer in the presence of the four deoxynucleotide triphosphates (one of which is radioactive) and DNA polymerase I (Klenow fragment) is now used as a primer on this nifH template to generate double stranded DNA (dsDNA). The mixture is incubated for 15-45 minutes at 25° to 37° C. during which time the complementary strand is substantially extended. The remaining single stranded DNA is then removed by digestion with S1 nuclease. EcoRI linkers (GGAATTCC) are then ligated to the double stranded DNA fragments followed by digestion with EcoRI. The fragments are separated by agarose gel electrophoresis and the fragment containing the promoter sequence is eluted and cloned into the wide host range plasmid pSUP204, which has previously been restricted by the restriction enzyme EcoRI. The resulting recombinant plasmid is termed pRjnifH-P/SS204. Following transformation and amplification in a suitable E. coli host strain, e.g., 17-1 which is restriction negative, i.e., r-, partial cleavage with EcoRI allows the addition of any foreign structural gene or foreign DNA fragment into the linearized plasmid downstream from the nifH promoter fragment. For example, the human prolactin gene can be inserted (Cooke, N. et al. (1981) J. Biol. Chem. 256:4007-4016) or the human metallothionein gene can be inserted (Karin, M. and R. I. Richards (1982) Nucleic Acids Res. 10:3165-3173) resulting in a "composite" recombinant. A composite recombinant is herein defined as a recombinant DNA plasmid containing a vector, a promoter sequence and any foreign DNA whose expression is under the control of said promoter sequence.

Following insertion of a foreign gene into linearized pSS204 or pSS104, the resulting co-integrated recombinant is transformed into a suitable E coli host strain, e.g., SM10 or RR1. Subsequently the co-integrated recombinant is transferred to a rhizobial species by bacterial conjugation using a helper plasmid such as RP4 if necessary. The rhizobial species carrying the co-integrated recombinant is then used to infect plants and later the root nodules are assayed for the production of foreign mRNA and/or protein by standard methods known in the art.

Insertion of the human metallothionein gene into the recombinant plasmid. Method II The procedure followed in this example is the same as that followed in the preceding example up to the point where EcoRI linkers are ligated to the double stranded DNA fragments followed by digestion with appropriate enzymes. The resultant DNA fragments are then cloned to cleaved pBR322. Following transformation and amplification in a suitable E. coli host strain, the recombinant plasmids are cleaved with appropriate enzymes and, if necessary, treated with S1 nuclease for a short time to remove the 3'-overhang. The recombinants are then cleaved with EcoRI and the double stranded nif regulatory fragment is cloned into cleaved pRK290 DNA. The resultant recombinant is thus a pRK290-nif-regulatory fragment construct. pRK290 is a wide host range plasmid.

The next step is to isolate DNA fragments carrying the foreign genes of interest and to ligate synthetic EcoRI linkers to these fragments. These modified fragments are then ligated into EcoRI cleaved vector DNA (i.e., the pRK290-nif promoter fragment construct) giving a "composite" recombinant (pRK290-nif promoter fragment-foreign gene) and transformed into an E. coli host strain, e.g., 17-1 or RR1. The composite recombinant is then transferred to a host species, e.g., Bradyrhizobium sp. (Parasponia) or B. japonicum, by bacterial conjugation using a helper plasmid whenever necessary. The bacteria carrying the composite recombinant are then used to infect plants, e.g., soybean or siratro, and later assayed for the production of foreign and/or protein by standard methods known in the art.

Insertion of the bacterial toxin gene from Bacillus thuringiensis into the recombinant plasmid Recombinant plasmids containing inserts of the gene encoding the toxic crystal protein of B. thurinoiensis are obtained using the techniques described (Wong, H. C., Schnepf, H. E. and H. R. Whiteley (1983) J. Biol. Chem. 258:1960–1967). The recombinant plasmid pES1 (ATCC Number 31995) consisting of the plasmid vector pBR322 and DNA homologous to the 30, 32 and 37 megadalton plasmids, as well as DNA homologous to linearized forms of the very large plasmids of B. thurinoiensis is partially cleaved with EcoRI to give linear molecules. These partial cleavage products are further restricted by the enzyme AvaI. The digestion conditions are as recommended by the manufacturer. A probe for the toxic crystal protein gene is isolated and radioactively labelled as previously described (Wong, H. C. et al. (1983) supra). The 15 kb fragment is then cloned into M13mp8 or M13mp9 according to standard procedures (Messing, J. and J. Vieira (1982) Gene 19:269–276) and transformed into E. coli JM103. The single stranded DNA from the extruded phage particles is purified and replicated in-vitro by use of a synthetic primer (5'-TGTTATCCATGGGTTACCTCC-3') (The general method of site specific mutagenesis is described in Zoller, M. J. and M. Smith (1982) Nucleic Acids Research 10:6587–7600). The resulting double stranded recombinant plasmid is then transformed back into E. coli JM103 and amplified. The amplified double stranded plasmid DNA is purified from the E. coli JM103 cells and cleaved with the restriction endonucleases NcoI and AvaI. NcoI cleaves at the site of the synthetic primer (which is the initiation site of the toxic crystal protein gene) and AvaI cleaves at a site which is downstream from the 3'-end of the toxic crystal protein gene. The overhangs are then filled in to blunt ends (Maniatis, T. et al. (1975) Proc. Nat. Acad. Sci. U.S.A. 72:1184–1188).

Finally, the recombinant plasmid which is derived from pSUP204 is cleaved with EcoRI and the overhangs filled in to blunt ends. HindIII linkers are then added to both the B. thurinoiensis toxic crystal protein gene fragment and to the SS204 recombinant Following the HindIII digestion of both components, the toxic crystal protein gene and the recombinant plasmid containing the nifD promoter region are ligated together to give a nifD promoter-B. thurinoiensis toxic crystal protein gene composite. The mixture is transformed into a suitable E. coli host, e.g., K802, SM10 or RR1. Plasmids are isolated from individual colonies and the orientation determined by restriction mapping. A colony containing a plasmid with the correct orientation is then conjugated to host bacteria and the plasmid is transferred as already described. The production of mRNA and/or the toxic crystal protein is monitored as already described (Wong, et al. supra).

Introduction of DNA sequences into the genome of gram-negative organisms other than E. coli This example is based on the following general principles. Two basic components are required. These are: (1) a suicide vector, and (2) a transposon.

Suicide vectors are plasmid molecules which replicate stably in one bacterial host (in this case, *Escherichia coli*) but fail to replicate in a different bacterial species (e.g., a Rhizobial species).

Transposons are genetic elements which are able to move (translocate) from one location to another in DNA. The translocation process is mediated by gene products encoded on the transposon and is dependent upon the integrity of repeated sequences (directly or indirectly repeated) located at each end of the transposon. Transposons generally carry a gene (or genes) encoding resistance to one or more antibiotics.

In the protocol to be outlined below, use is made of the transposon designated Tn5 and the suicide vector pSUP1011 (Simon, R. et al. (1981) Proc. of Bielefeld Symposium, Springer-Verlag, West Germany).

Transposon Tn5 is a DNA element of 5.7 kilobases (kb) in length, consisting of 1.5 kb inverted repeat sequences flanking a 2.7 kb central region. Encoded within one of the inverted repeats are the functions required for transposition. The central region of the transposon carries a gene conferring resistance to the antibiotic kanamycin ($km^r$). In the middle of the central region is a DNA sequence which is recognized by the restriction endonuolease BamHI. In the suicide vector pSUP1011, the only site recognized and cut by BamHI is that located within the Tn5 element. Experiments (Simon, R. et al. (1983) Proc. of Bielefeld Symposium, Springer-Verlag, West Germany) have shown that insertion of DNA fragments into the BamHI site of Tn5 does not disrupt normal transposition nor expression of the kanamycin-resistance gene of the resultant "hybrid" transposon.

The DNA fragment to be introduced can be generated in a number of ways:

(1) Complete or partial restriction with BamHI, Sau3A, MboI, etc. which generate fragments having the same, complementary, single-stranded ends.
(2) Partial or complete digestion with restriction endonucleases which generate DNA fragments having blunt ends.
(3) Digestion of DNA with the enzyme DNAse I in the presence of $Mn^{++}$ ions which generates random fragments which (generally) are blunt ended.

The suicide vector (pSUP1011) DNA is treated as follows depending on the type of fragment to be cloned (above):

(1) Complete restriction with endonuclease BamHI and treatment with the enzyme alkaline phosphatase.
(2) Complete restriction with BamHI followed by either:
 (a) treatment with S1 nuclease to remove the single-stranded ends, or
 (b) "filling in" of the single-stranded ends by the enzyme reverse transcriptase in the presence of nucleotide triphosphates.

Each of the above treatments is followed by treatment with alkaline phosphatase.

Cloning: Vector and fragment DNA, prepared as above, are mixed and treated with the enzyme T4 DNA ligase. The ligated DNA is then transformed (introduced) into *Escherichia coli* strain SM10. (This strand is capable of mobilizing (Mob+) pSUP1011 derivatives (recombinant plasmids) into other gram-negative bacteria.) (Simon, R. et al. (1983) Proc. of Bielefeld Symposium, Springer-Verlag, West Germany). The resultant transformants are screened by the Grunstein and Hogness colony hybridization procedure (Grunstein, M. and D. S. Hogness (1975) Proc. Natl. Acad. Sci. U.S.A. 72:3961) to detect those containing the desired cloned DNA fragment.

Introduction of the cloned DNA fragment into the genome of any gram-negative bacterium is achieved via a process called bacterial conjugation. The E. coli SM10 derivative, carrying the desired pSUP1011 recombinant, is mixed with cells of (kanamycin-sensitive) gram-negative bacteria on the surface of a nutrient agar plate. The plate is incubated for a period (4-16 hours) at 29°-30° C. and during this time cells of each type come into physical contact (conjugation) and the pSUP1011 derivative is transferred from E. coli to the host gram-negative bacteria. The cell mixture is washed off the plate and spread on an agar plate which is selective for kanamycin-resistant host bacteria. The resultant colonies will be derivatives of the host bacteria in which the cloned DNA fragment, within Tn5, will be inserted at some point in the genome. Selection for kanamycin resistance ensures maintenance of the inserted DNA.

At this stage it is unknown whether the DNA fragment, within Tn5, has been transferred to the chromosome of the host bacteria or to one of its several plasmids. This uncertainty can be resolved by visualization of the plasmids and the bacterial chromosome by ethidium bromide staining after horizontal agarose gel electrophoresis (Djordjevic, M. A. et al. (1982) J. Bacteriol. 151:560-568).

The following bacteria strain was deposited at the Northern Regional Research Center, U.S. Department of Agriculture, 1815 North University Street, Peoria, Illinois 61604, USA:

E. coli RR1/pPR289nif-2

The date of the deposit was June 17, 1983, and the accession number is NRRL B-15446.

The following plasmid was deposited with the American Type Culture Collection, 12301 Parklawn Drive, Rockville, Maryland 20852, USA:

pPR289nif-2

The date of the deposit was June 17, 1983, and the accession number is 40073.

We claim:

1. A method for expressing a foreign structural gene under control of a promoter capable of activating a nifH gene in a nodule selected from the group consisting of:
   (1) the sequence of the Bradyrhizobium sp. (Parasponia) nifH promoters as follows:

5'... CCG CGC AGA TCC TGT CCG GTG CAA ACC TCC

CTG GGG TAG CTC AGC GGC TCG TTG GCT TTT TAG

AGC GTA ATC AAG AAG CTT AAT AAG CGC GGA CAG

TGT TGG CAT GGC GAT TGC TGT TGA GTT GCA GCA

ACA CTG AGT GAG GGC TGG GTG CAC GCC GAC GCG

TAA GAC GAG CGA TGC GCT CCT TCC CTT GAA CCC

GTG TGC CCC GTT TCT GAG AGA GAA ACA AGC TCG

CGT GTC GGA AGC ACG CAA CTT TTG GCA AAT CGG

TTG ATG GAG AAC AAC ATG ... 3'; and (2) the sequence of the *Bradyrhizobium japonicum* nifH regulatory region as follows:

5'... TTT GGC TGT TGG CGT TCA TGT TTG CGA TTG

TTT GTT CGT TGT CTG ACA GCC GGG CAG ATC TTG

TCA GAT CCA AAA CAG CCT ACG ATC GCG CGC CGG

CTG GTT GCT TTT GGA AAC GTA ATC AGA AGC TTA

AGG TGC CGG GTT AGA CCT TGG CAC GGC TGT TGC

TGA TAA GCG GCA GCA ACA CTG AGT GAG GGC TGA

GTG CAC GCC GAC GTG TAA GGC GAG CGA TGC GCT

CCT TCC CTT GAA CCC GTG TGC CCC CGT TTC TGC

GAG GGA AGC AAA GCT CGC AAA AGA AGC GCG CAA

CGT TTG GCA AAT CGG TTG ATG GAG AGC AGC ... 3';

which method comprises:
   (a) introducing a DNA molecule comprising a foreign structural gene under control of said promoter into a rhizobial strain capable of forming nodules on a plant; and
   (b) infecting a plant with said rhizobial strain wherein nodules are formed and expression of mRNA or protein coded by said foreign structural gene occurs within said nodules.

2. A recombinant DNA molecule comprising:
   (a) a promoter, capable of activating expression of a nifH gene in a nodule of a plant, and having a nucleotide sequence selected from the group consisting of a nucleotide sequence from the Bradyrhizobium sp. (Parasponia) nifH promoter as follows:

5'... CCG CGC AGA TCC TGT CCG GTG CAA ACC TCC

CTG GGG TAG CTC AGC GGC TCG TTG GCT TTT

TAG AGC GTA ATC AAG AAG CTT AAT AAG CGC

GGA CAG TGT TGG CAT GGC GAT TGC TGT TGA

GTT GCA GCA ACA CTG AGT GAG GGC TGG GTG

CAC GCC GAC GCG TAA GAC GAG CGA TGC GCT

CCT TCC CTT GAA CCC GTG TGC CCC GTT TCT

GAG AGA GAA ACA AGC TCG CGT GTC GGA AGC

ACG CAA CTT TTG GCA AAT CGG TTG ATG GAG

AAC AAC ATG ... 3';

and a nucleotide sequence from the *Bradyrhizobium japonicum* nifH promoter as follows:

5'... TTT GGC TGT TGG CGT TCA TGT TTG CGA TTG

-continued

TTT GTT CGT TGT CTG ACA GCC GGG CAG ATC TTG

TCA GAT CCA AAA CAG CCT ACG ATC GCG CGC CGG

CTG GTT GCT TTT GGA AAC GTA ATC AGA AGC TTA

AGG TGC CGG GTT AGA CCT TGG CAC GGC TGT

TGC TGA TAA GCG GCA GCA ACA CTG AGT GAG

GGC TGA GTG CAC GCC GAC GTG TAA GGC GAG

CGA TGC GCT CCT TCC CTT GAA CCC GTG TGC

CCC CGT TTC TGC GAG GGA AGC AAA GCT CGC

AAA AGA AGC GCG CAA CGT TTG GCA AAT CGG

TTG ATG GAG AGC AGC . . . 3'; and (b) a foreign structural gene under control of said promoter.

3. A plasmid comprising the DNA molecule of claim 2.

4. The DNA molecule of claim 2 in which the foreign structural gene is a bacterial toxin gene of *Bacillus thuringiensis*.

5. A bacterial strain comprising the DNA molecule of claim 2.

6. The recombinant DNA molecule of claim 2 comprising:
(a) a promoter, capable of activating expression of a Bradyrhizobium sp. (Parasponia) nifH gene in a nodule of a plant, and having a nucleotide sequence comprising the Bradyrhizobium sp. (Parasponia) nifH promoter as follows:

5' . . . CCG CGC AGA TCC TGT CCG GTG CAA ACC TCC

CTG GGG TAG CTC AGC GGC TCG TTG GCT TTT

TAG AGC GTA ATC AAG AAG CTT AAT AAG CGC

GGA CAG TGT TGG CAT GGC GAT TGC TGT TGA

GTT GCA GCA ACA CTG AGT GAG GGC TGG GTG

CAC GCC GAC GCG TAA GAC GAG CGA TGC GCT

CCT TCC CTT GAA CCC GTG TGC CCC GTT TCT

GAG AGA GAA ACA AGC TCG CGT GTC GGA AGC

ACG CAA CTT TGC GCA AAT CGG TTG ATG GAG

AAC AAC ATG . . . 3'; and (b) a foreign structural gene under control of said promoter.

7. The recombinant DNA molecule of claim 2 comprising:
(a) a promoter, capable of activating expression of a *Bradyrhizobium japonicum* nifH gene in a nodule of a plant, and having a nucleotide sequence comprising the *Bradyrhizobium japonicum* nifH promoter as follows:

5' . . . TTT GGC TGT TGG CGT TCA TGT TTG CGA TTG

TTT GTT CGT TGT CTG ACA GCC GGG CAG ATC TTG

TCA GAT CCA AAA CAG CCT ACG ATC GCG CGC CGG

CTG GTT GCT TTT GGA AAC GTA ATC AGA AGC TTA

AGG TGC CGG GTT AGA CCT TGG CAC GGC TGT

TGC TGA TAA GCG GCA GCA ACA CTG AGT GAG

GGC TGA GTG CAC GCC GAC GTG TAA GGC GAG

CGA TGC GCT CCT TCC CTT GAA CCC GTG TGC

CCC CGT TTC TGC GAG GGA AGC AAA GCT CGC

AAA AGA AGC GCG CAA CGT TTG GCA AAT CGG

TTG ATG GAG AGC AGC . . . 3'; and (b) a foreign structural gene under control of said promoter.

* * * * *

UNITED STATES PATENT AND TRADEMARK OFFICE
CERTIFICATE OF CORRECTION

PATENT NO. : 5,008,194

DATED : April 16, 1991

INVENTOR(S) : Barry G. Rolfe, et al

It is certified that error appears in the above-identified patent and that said Letters Patent is hereby corrected as shown below:

Column 2, line 47, rewrite "(1981 In" as --(1981) In--.

Column 4, line 48, rewrite "In:" as --In--.

Column 6, line 19, rewrite "Vol.21D" as --Vol. 21D--.

Column 6, line 42, rewrite "genome A" as --genome. A--.

Column 8, line 35, rewrite "thurinoiensis" as --thuringiensis--.

Column 9, line 38, rewrite "the gene" as --the nifH gene--

Column 11, line 32, rewrite "positivelyhybridizing" as --positively-hybridizing--.

Column 11, line 40, rewrite "pBR32" as --pBR332--.

Column 12, line 4, rewrite "Cell 15 20:269-281)" as --Cell 20:269-281)--.

Column 12, line 42, rewrite "α-subunit" as --ß-subunit--.

Column 14, line 15, insert --B. japonicum nifDK operon (see Figure 1 for a comparison of B. japonicum nifDK and nifH).-- after "the".

UNITED STATES PATENT AND TRADEMARK OFFICE
CERTIFICATE OF CORRECTION

PATENT NO. : 5,008,194

DATED : April 16, 1991

INVENTOR(S) : Barry G. Rolfe, et al

It is certified that error appears in the above-identified patent and that said Letters Patent is hereby corrected as shown below:

Column 14, line 59, rewrite "136:267-2179" as --136:267-279--.

Column 15, line 48, rewrite "promoter, can" as --promoter can--.

Column 17, line 22, rewrite "1983,now" as --1983, now--.

Column 18, line 61, bridging lines 61-62, rewrite "sitespecific" as --site-specific--.

Column 19, line 13, insert --,-- between "8.0" and "1".

Column 19, line 21, rewrite "-20.C." as -- -20°C.--.

Column 19, line 46, rewrite "plasmid" as --Plasmid--.

Column 19, line 65, rewrite "dATP, and dTTP" as --dATP and dTTP,--.

Column 20, line 22, rewrite "pH8.1" as --pH 8.1--.

Column 20, line 64, rewrite "jaconicum" as --B. japonicum--.

UNITED STATES PATENT AND TRADEMARK OFFICE
CERTIFICATE OF CORRECTION

PATENT NO. : 5,008,194

DATED : April 16, 1991

INVENTOR(S) : Barry G. Rolfe, et al

It is certified that error appears in the above-identified patent and that said Letters Patent is hereby corrected as shown below:

Column 23, line 12, insert --mRNA-- before "and/or".

Column 23, line 17, rewrite "thurinoiensis" as --thuringiensis--.

Column 23, line 25, rewrite "thurinoiensis as --thuringiensis--.

Column 23, line 56, rewrite "thurinoiensis" as --thuringiensis--.

Column 23, line 57, rewrite "recombinant Following" as --recombinant. Following--.

Column 24, line 34, rewrite "endonuolease" as --endonuclease--.

Signed and Sealed this

Seventh Day of June, 1994

BRUCE LEHMAN

Attest:

Attesting Officer

Commissioner of Patents and Trademarks